United States Patent [19]

Yu et al.

[11] 4,258,052

[45] Mar. 24, 1981

[54] TREATMENT OF PSORIASIS WITH NICOTINAMIDE ANALOGUES

[76] Inventors: Ruey J. Yu, 4 Lindenwold Ave., Ambler, Pa. 19002; Eugene J. Van Scott, 1138 Sewell La., Rydal, Pa. 19046

[21] Appl. No.: 9,589

[22] Filed: Feb. 5, 1979

Related U.S. Application Data

[63] Continuation-in-part of Ser. No. 715,131, Aug. 17, 1976, Pat. No. 4,141,977, which is a continuation-in-part of Ser. No. 601,411, Aug. 4, 1975, Pat. No. 4,067,975.

[51] Int. Cl.³ .......................................... A61K 31/455
[52] U.S. Cl. ................................................. 424/266
[58] Field of Search ........................................ 424/266

[56] References Cited
U.S. PATENT DOCUMENTS 4,082,846   4/1978   Clark ................................. 424/266

OTHER PUBLICATIONS

Chemical Abstracts, 66, 84597y (1967).
Chemical Abstracts, 67, 43650n (1967).
Chemical Abstracts, 75, 35630j (1971).

Primary Examiner—Leonard Schenkman
Attorney, Agent, or Firm—Le Blanc, Nolan, Shur & Nies

[57] ABSTRACT

A treatment to alleviate the symptoms of psoriasis consisting of topical application of a cream, lotion, ointment or gel containing as the principal active ingredient one or more nicotinamide analogues is disclosed. The therapeutic composition may include a single member of the above active ingredients present in a total amount of from 0.01 to 5 percent by weight of the total composition or a plurality thereof present in a preferred concentration range of from 0.02 to 2 percent by weight of the total composition. Topical application of the therapeutic composition in a cream, ointment, lotion, water or gel has been found to achieve from substantial to complete remissions of psoriasis in humans.

23 Claims, No Drawings

TREATMENT OF PSORIASIS WITH NICOTINAMIDE ANALOGUES

This application is a continuation-in-part of our U.S. Patent Application Ser. No. 715,131, filed Aug. 17, 1976, now U.S. Pat. No. 4,141,977 which application is a continuation-in-part of U.S. Patent Application Ser. No. 601,411, filed Aug. 4, 1975, now U.S. Pat. No. 4,067,975.

This application relates to a treatment of the symptoms of psoriasis and specifically to three classes of nicotinamide analogues found to be effective thereof.

In our prior Patent Application Ser. No. 715,131 it was disclosed that certain 6-substituted nicotinamides and 2-substituted pyrazinamides were effective in treating the symptoms of psoriasis by topical application. In our parent case, U.S. Pat. No. 4,067,975, the use of 6-aminonicotinamide and thionicotinamide in compositions for the treatment of psoriasis was disclosed. It has now been discovered that many additional related compounds are also effective as will be subsequently described.

In accordance with the present invention, the nicotinamide analogues which are incorporated in therapeutic compositions for topical application to alleviate the symptoms of psoriasis are grouped in the following three classes:

The first class of compounds are 6-substituted nicotinamides, as shown by the following chemical structures:

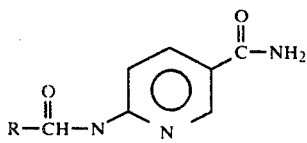

R: an alkyl, aryl, phosphoryl or acyl of 1 to 9 carbon atoms; a salt form or an ester form with 1 to 9 carbon atoms of the acyl group.

Preferred 6-substituted nicotinamides which are useful for the topical treatment of psoriasis are listed below:
1. 6-Acetylamino nicotinamide
2. 6-Benzoylamino nicotinamide
3. 6-Oxalylamino nicotinamide and its salts
4. 6-Malonylamino nicotinamide and its salts
5. 6-Succinylamino nicotinamide and its salts
6. 6-Glutarylamino nicotinamide and its salts
7. 6-Succinylamino nicotinamide methyl ester
8. 6-Glutarylamino nicotinamide methyl ester
9. 6-Succinylamino nicotinamide ethyl ester
10. 6-Succinylamino nicotinamide isoamyl ester
11. 6-Glutarylamino nicotinamide ethyl ester
12. 6-Glutarylamino nicotinamide isoamyl ester
13. 6-Maleylamino nicotinamide and its ester
14. 6-Phthalylamino nicotinamide and its ester
15. 6-Phosphorylamino nicotinamide and its ester
16. 6-Diphenylphosphorylamino nicotinamide and its ester.

The second class of compounds are 1,6-disubstituted 1,6-dihydronicotinamide and its analogues, as shown by the following chemical structure.

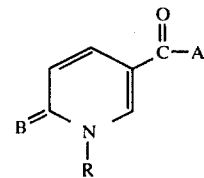

R: an alkyl or aryl of 1 to 9 carbon atoms
A: OH, $NH_2$, or an alkoxy of 1 to 9 carbon atoms
B: O or NH Preferred 1,6-disubstituted 1,6-dihydronicotinamide and its analogues which are useful for the topical treatment of psoriasis are listed below:
1. 1-Methyl-6-keto-1,6-dihydronicotinamide
2. 1-Methyl-6-keto-1,6-dihydronicotinic acid
3. Methyl 1-methyl-6-keto-1,6-dihydronicotinate
4. Ethyl 1-methyl-6-keto-1,6-dihydronicotinate
5. 1-Phenyl-6-keto-1,6-dihydronicotinamide
6. 1-Phenyl-6-keto-1,6-dihydronicotinic acid
7. Methyl 1-phenyl-6-keto-1,6-dihydronicotinate
8. Ethyl 1-phenyl-6-keto-1,6-dihydronicotinate
9. 1-Benzyl-6-keto-1,6-dihydronicotinamide
10. 1-Benzyl-6-keto-1,6-dihydronicotinic acid
11. Methyl 1-benzyl-6-keto-1,6-dihydronicotinate
12. Ethyl 1-benzyl-6-keto-1,6-dihydronicotinate
13. 1-Methyl-6-imino-1,6-dihydronicotinamide
14. 1-Phenyl-6-imino-1,6-dihydronicotinamide
15. 1-Benzyl-6-imino-1,6-dihydronicotinamide
16. Methyl 1-methyl-6-imino-1,6-dihydronicotinate
17. Methyl 1-phenyl-6-imino-1,6-dihydronicotinate
18. Methyl 1-benzyl-6-imino-1,6-dihydronicotinate The third class of nicotinamide derivatives is a 1 substituted -6-amino-1,2-dihydronicotinamide and its analogues, as shown by the following chemical structure:

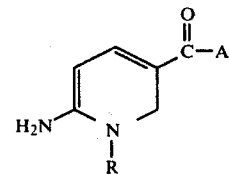

R: an alkyl or aryl of 1 to 9 carbon atoms
A: OH, $NH_2$, or an alkoxy of 1 to 9 carbon atoms Preferred 1 substituted -6-amino-1,2-dihydronicotinamide and its analogues which are useful for the topical treatment of psoriasis are listed below:
1. 1-Methyl-6-amino-1,2-dihyrodnicotinamide
2. 1-Methyl-6-amino-1,2-dihydronicotinic acid
3. Methyl 1-methyl-6-amino-1,2-dihydronicotinate
4. Ethyl 1-methyl-6-amino-1,2-dihydronicotinate
5. 1-Phenyl-6-amino-1,2-dihydronicotinamide
6. 1-Phenyl-6-amino-1,2-dihydronicotinic acid
7. Methyl 1-phenyl-6-amino-1,2-dihydronicotinate
8. Ethyl 1-phenyl-6-amino-1,2-dihydronicotinate
9. 1-Benzyl-6-amino-1,2-dihydronicotinamide
10. 1-Benzyl-6-amino-1,2-dihydronicotinic acid
11. Methyl 1-benzyl-6-amino-1,2-dihydronicotinate
12. Ethyl 1-benzyl-6-amino-1,2-dihydronicotinate Accordingly, it is an object of this invention to provide new compounds which are nicotinamide derivatives and are useful in treating the symptoms of psoriasis by topical application in a pharmaceutically accepted vehicle.

It is another object of this invention to provide a class of 6-substituted nicotinamides and related compounds useful in treating psoriasis when incorporated in a medicinal composition for topical application.

It is another object of this invention to provide a class of 1,6-disubstituted 1,6-dihydronicotinamides and related compounds useful in treating psoriasis when incorporated in a medicinal composition for topical application.

It is still another object of this invention to provide a class of 1 substituted-6-amino-1,2-dihydronicotinamides and related compounds useful in treating psoriasis when incorporated in a medicinal composition for topical application.

These and other objects will become readily apparent with reference to the following description:

The following examples describe methods for synthesizing representative compounds of this invention, a vehicle therefor, and therapeutic compositions formulated with representative compounds. These examples then are not intended to be limitative of the scope of this invention but rather illustrative thereof.

EXAMPLE 1

Synthesis of 6-Succinylamino nicotinamide

6-Amino nicotinamide 13.7 g (0.1 mole) is dissolved in 100 ml of dimethylsulfoxide and succinic anhydride 15 g (0.15 mole) is added to the above solution. The mixture is heated to 50° C. for 3 hours, then is admixed with a solution of methyl alcohol 200 ml and calcium chloride 20 g. The white precipitate is isolated by filtration and is purified by washing with 0.2 N HCl and ethanol. 6-Succinylamino nicotinamide 15.4 g thus synthesized is practically pure as shown by infrared spectroscopy and by thin-layer chromatography.

EXAMPLE 2

Synthesis of 6-Glutarylamino nicotinamide

6-Amino nicotinamide 13.7 g (0.1 mole) is dissolved in 137 ml of dimethylsulfoxide and glutaric anhydride 17 g (0.15 mole) is added to the above solution. The mixture is heated to 50° C. for 3 hours, then is admixed with a solution of methyl alcohol 200 ml and calcium chloride 20 g. The white precipitate is isolated by filtration and is purified by washing with 0.2 N HCl and ethanol. 6-Glutarylamino nicotinamide 15 g thus synthesized is practically pure as shown by infrared spectroscopy and thin-layer chromatography.

EXAMPLE 3

6-Succinylamino nicotinamide 1% cream is prepared as follows:

6-Succinylamino nicotinamide powder 1 g is directly mixed with 99 g of hydrophilic ointment USP. The mixing is continued until a uniform consistency is obtained.

EXAMPLE 4

A water-in-oil cream may be prepared as follows:
Part A:
  Sorbitan sesquioleate: 2 g
  Petrolatum: 10 g
  Mineral oil: 15 g
  Beeswax: 10 g
  Isopropyl myristate: 10 g
  Squalene: 5 g
  Tocopheryl acetate: 5 g
Part B:
  Water: 34 ml
  Sorbitol: 3 g
  Propylene glycol: 5 g
  Magnesium oxide: 0.2 g Heat Part A to 75° C. and heat Part B to 80° C. Add Part B slowly to Part A with agitation. Continue agitation until the mixture is congealed. Similar water-in-oil creams are disclosed in our U.S. Patent Application Ser. No. 888,938, filed Mar. 22, 1978, the disclosure of which is hereby incorporated by reference.

EXAMPLE 5

6-Succinylamino nicotinamide 1% in water-in-oil cream is prepared as follows:

6-Succinylamino nicotinamide powder 1 g is directly mixed with 99 g of water-in-oil cream prepared according to Example 4. Mixing is continued until a uniform consistency is obtained.

EXAMPLE 6

6-Glutarylamino nicotinamide 1% cream is prepared as follows:

6-Glutarylamino nicotinamide powder 1 g is directly mixed with 99 g of hydrophilic ointment USP. Mixing is continued until a uniform consistency is obtained.

EXAMPLE 7

6-Glutarylamino nicotinamide 1% in water-in-oil cream is prepared as follows:

6-Glutarylamino nicotinamide powder 1 g is directly mixed with 99 g of water-in-oil cream prepared according to Example 4. Mixing is continued until a uniform consistency is obtained.

EXAMPLE 8

Synthesis of 6-Maleylamino nicotinamide

6-Amino nicotinamide 13.7 g (0.1 mole) is dissolved in 100 ml of dimethylsulfoxide and maleic anhydride 14.7 g (0.15 mole) is added to the above solution. The mixture is stirred at room temperature for 16 hours, then is admixed with a solution of methyl alcohol 200 ml and calcium chloride 20 g. The white precipitate is isolated by filtration and is purified by washing with 0.2 N HCl and ethanol. 6-Maleylamino nicotinamide thus synthesized is practically pure as shown by infrared spectroscopy and thin-layer chromatography.

EXAMPLE 9

Synthesis of 6-Phthalylamino nicotinamide

6-Amino nicotinamide 13.7 g (0.1 mole) is dissolved in 100 ml of dimethylsulfoxide and phtalic anhydride 19.2 g (0.13 mole) is added to the above solution. The mixture is stirred at room temperature for 16 hours, then is admixed with a solution of 500 ml methanol and 500 ml water. The white precipitate is isolated by filtration and is purified by washing with 0.2 N HCl and methanol. 6-Phthalylamino nicotinamide thus synthesized is practically pure as shown by infrared spectroscopy and thin-layer chromatography.

EXAMPLE 10

Synthesis of 6-Acetylamino nicotinamide

6-Amino nicotinamide 13.7 g (0.1 mole) is dissolved in 100 ml of dimethylsulfoxide and acetic anhydride 14.2 ml (0.15 mole) is added to the above solution. The mixture is stirred at room temperature for 16 hours. White crystals which are formed during the reaction are isolated by filtration and are purified by washing with 0.2 N HCl and ethanol. 6-Acetylamino nicotinamide 9.5 g thus synthesized is practically pure as shown by infrared spectroscopy and thin-layer chromatography.

EXAMPLE 11

6-Maleylamino nicotinamide 0.2% cream is prepared as follows:

6-Maleylamino nicotinamide powder 0.2 g is directly mixed with 99.8 g of hydrophilic ointment USP. The mixing is continued until a uniform consistency is obtained.

EXAMPLE 12

6-Maleylamino nicotinamide 0.5% in water-in-oil cream is prepared as follows:

6-Maleylamino nicotinamide powder 0.5 g is directly mixed with 99.5 g of water-in-oil cream prepared according to Example 4. The mixing is continued until a uniform consistency is obtained.

EXAMPLE 13

6-Phthalylamino nicotinamide 1% cream is prepared as follows:

6-Phthalylamino nicotinamide powder 1 g is directly mixed with 99 g of hydrophilic ointment USP. The mixing is continued until a uniform consistency is obtained.

EXAMPLE 14

6-Phthalylamino nicotinamide 1% in water-in-oil cream is prepared as follows:

6-Phthalylamino nicotinamide powder 1 g is directly mixed with 99 g of water-in-oil cream prepared according to Example 4. The mixing is continued until a uniform consistency is obtained.

EXAMPLE 15

6-Acetylamino nicotinamide 0.5% cream is prepared as follows:

6-Acetylamino nicotinamide powder 0.5 g is directly mixed with 99.5 g of hydrophilic ointment USP. The mixing is continued until a uniform consistency is obtained.

EXAMPLE 16

6-Acetylamino nicotinamide 0.5% in water-in-oil cream is prepared as follows:

6-Acetylamino nicotinamide powder 0.5 g is directly mixed with 99.5 g of water-in-oil cream prepared according to Example 4. The mixing is continued until a uniform consistency is obtained.

EXAMPLE 17

Synthesis of 6-Diphenylphosphorylamino nicotinamide

6-Aminonicotinamide 1.37 g (0.01 mole) is dissolved in 10 ml of 2-pyrrolidinone and 3 ml of pyridine by gentle warming of the mixture. Diphenylphosphoryl chloride 6 ml (0.024 mole) is then slowly added to the mixture. After 1 hour of reaction at room temperature, the mixture is poured into 300 ml of 0.2 N HCl. A reddish syrup, 2.2 g which is formed in the bottom of the flask is isolated by decantation. The product may be purified as follows. The reddish syrup obtained above is dissolved in 3 ml of ethanol and the solution is admixed with 200 ml of 0.2 N HCl. Chloroform, 100 ml is added to the mixture to extract the product. After dried over anhydrous sodium sulfate the chloroform solution which contains the product is evaporated at 35° C. in vacuum to give a practically pure 6-diphenylphosphorylamino nicotinamide.

EXAMPLE 18

Synthesis of Methyl 1-methyl-6-keto-1,6-dihydronicotinate

6-Hydroxy nicotinic acid 42 g (0.3 mole) is added portionwise to dimethylsulfate, 95 ml (1 mole) at 60°–70° C. The mixture is heated to 80°–85° C. for 2 hours to complete the N-methylation. After the addition of anhydrous methanol, 200 ml the mixture is heated at 65° C. for 5 hours. The reaction mixture is cooled with ice-water bath and 4 N NaOH 250 ml is added slowly to the mixture until $pH_8$ is obtained. The white solid product, 30 g, thus formed is collected by filtration and washed with benzene. Methyl 1-methyl-6-keto-1,6-dihydronicotinate thus synthesized may be purified as follows. The white solid product as obtained above is dissolved in 200 ml of chloroform. A small amount of insoluble material is removed by filtration. The filtrate which contains pure compound is evaporated at 40° C. in a vacuum to give a white crystalline compound which is washed with ether and is dried.

Methyl 1-methyl-6-keto-1,6-dihydronicotinate thus synthesized is practically pure as shown by infrared spectroscopy and thin-layer chromatography with a mobility of 0.76 on a solvent system of benzene:methanol, 1:1.

EXAMPLE 19

Synthesis of 1-methyl-6-keto-1,6-dihydronicotinic acid

Methyl 1-methyl-6-keto-1,6-dihydronicotinate 3 g synthesized according to Example 18 is suspended in 20 ml of 1 N NaOH. The mixture is heated to 100° C. for 5 minutes to complete the hydrolysis. The clear solution thus obtained is neutralized to pH4 with 4 N HCl. The white crystalline product thus formed is isolated by filtration. 1-Methyl-6-keto-1,6-dihydronicotinic acid thus synthesized is practically pure as shown by infrared spectroscopy and thin-layer chromatography with a mobility of 0.70 on a solvent system of benzene:methanol, 1:1.

EXAMPLE 20

Methyl 1-methyl-6-keto-1,6-dihydronicotinate 1% cream is prepared as follows.

Methyl 1-methyl-6-keto-1,6-dihydronicotinate 1 g synthesized according to Example 18 is dissolved in 5 ml of 2-pyrrolidinone and the solution is admixed with 94 g of hydrophilic ointment USP. Mixing is continued until a uniform consistency is obtained.

EXAMPLE 21

Methyl 1-methyl-6-keto-1,6-dihydronicotinate 2% water-in-oil cream is prepared as follows.

Methyl 1-methyl-6-keto-1,6-dihydronicotinate 2 g is dissolved in 10 ml of 2-pyrrolidinone, and the solution is admixed with 88 g of water-in-oil cream prepared according to Example 4. Mixing is continued until a uniform consistency is obtained.

EXAMPLE 22

6-Diphenylphosphorylamino nicotinamide 1% cream is prepared as follows.

6-Diphenylphosphorylamino nicotinamide 1 g synthesized according to Example 17 is directly admixed with 99 g of hydrophilic ointment USP. The mixing is continued until a uniform consistency is obtained.

EXAMPLE 23

1-Methyl-6-keto-1,6-dihydronicotinic acid 1% cream is prepared as follows.

1-Methyl-6-keto-1,6-dihydronicotinic acid 1 g synthesized according to Example 19 is dissolved with 10 ml of 2-pyrrolidinone, and the solution is admixed with 89 g of hydrophillic ointment USP. Mixing is continued until a uniform consistency is obtained.

EXAMPLE 24

Synthesis of 1-methyl-6-amino-1,2-dihydronicotinamide

There are two steps involved in the synthesis of 1-methyl-6-amino-1,2-dihydronicotinamide. 6-Aminonicotinamide 42 g (0.3 mole) is added portionwise to dimethylsulfate 70 ml. The mixture is heated at 100° C. for 2 hours. A sticky product thus obtained is poured into 500 g of ice. The mixture is filtered to remove some insoluble materials. Sodium carbonate is then added to the filtrate until the mixture has pH9. White precipitate thus formed is isolated by filtration and is washed with water and acetone. 1-Methyl-6-amino-nicotinamide salt 17 g thus synthesized is utilized for the following second step of synthesis.

1-Methyl-6-aminonicotinamide salt 5 g synthesized above is dissolved in 50 ml of 1 N HCl. Platinum dioxide 0.1 g is added to the solution and the mixture is hydrogenated at room temperature for 3 hours. The mixture is filtered to remove platinum and the filtrate is neutralized with 4 N NaOH to pH8. The filtrate is concentrated to approximately 20 ml by evaporation of water at 40° C. in vacuum. White crystals thus formed are isolated by filtration and are washed with water. 1-Methyl-6-amino-1,2-dihydronicotinamide 1.7 g thus synthesized is practically pure as shown by infrared spectroscopy and by thin-layer chromatography.

EXAMPLE 25

1-Methyl-6-amino-1,2-dihydronicotinamide 1% cream is prepared as follows.

1-Methyl-6-amino-1,2-dihydronicotinamide 1 g synthesized according to Example 24 is dissolved in 10 ml of 2-pyrrolidinone and the solution is admixed with 89 g of hydrophilic ointment USP. The mixing is continued until a uniform consistency is obtained.

EXAMPLE 26

Synthesis of 1-phenyl-6-keto-1,6-dihydronicotinic acid

The following procedure may be utilized for the syntheses of 1-aryl-6-keto-1,6-dihydronicotinic acids and esters thereof. The procedure is a unique application conceptualized, from a basic method of synthesis for 6-keto-1,6-dihydronicotinic acid and esters thereof from coumalic acid and ammonia as described in Organic Syntheses Collective Volume 5 page 532–534 (1967).

Coumalic acid 16 g (0.1 mole) is slowly added to a mixture of aniline 50 ml (0.55 mole) and water 250 ml. As will be obvious to those skilled in the art, aniline analogues benzyl amine and phenyl ethyl amines could be used depending on the end product desired. The mixture is stirred in a cold water bath for 5 hours. A brownish syrupy product formed in the bottom of the reaction flask is isolated by decantation off the supernatant and is washed three times with water (3×200 ml). The syrupy product is dissolved in 300 ml of methanol, and the methanol solution is filtered to remove small amounts of insoluble materials. The filtrate is then poured slowly into 1,200 ml of 5% acetic acid in water. Light yellowish precipitates thus formed are isolated by filtration and are washed with water and dried in a vacuum. 1-Phenyl-6-keto-1,6-dihydronicotinic acid 12 g thus synthesized is identified by both infrared spectroscopy and thin-layer chromatography with a mobility of 0.73 on a solvent system of benzene:methanol, 1:1.

EXAMPLE 27

1-Phenyl-6-keto-1,6-dihydronicotinic acid 2% cream is prepared as follows:

1-Phenyl-6-keto-1,6-dihydronicotinic acid 2 g synthesized according to Example 26 is dissolved in 10 ml of 2-pyrrolidinone, and the solution is admixed with 88 g of hydrophilic ointment USP. The mixing is continued until a uniform consistency is obtained.

EXAMPLE 28

1-Phenyl-6-keto-1,6-dihydronicotinic acid 5% water-in-oil cream is prepared as follows:

1-Phenyl-6-keto-1,6-dihydronicotinic acid 5 g is dissolved in 15 ml of 2-pyrrolidinone, and the solution is admixed with 80 g of water-in-oil cream. The mixing is continued until a uniform consistency is obtained.

TEST RESULTS

In order to evaluate the compounds of this invention a total of more than 15 patients having psoriasis was tested with the composition as follows:

Therapeutic compositions containing 0.2%, 0.5% and 1% nicotinamide analogues of this invention in either hydrophilic ointment USP or water-in-oil cream prepared according to the foregoing Examples were topically administered to patients having psoriasis.

Test areas were kept to minimal size convenient for topical application, i.e. circles approximately 4 cm in diameter. The medicinal creams or ointments were topically applied by the patient in an amount (usually about 0.1 cubic millimeter) sufficient to cover the test site. Applications were made three times daily and without occlusive dressings. Test periods did not exceed two weeks, and applications were discontinued at any time when resolution of the lesion on the test area was clinically judged to be complete.

TABLE

| Compound | Number of Patients | Therapeutic Effectiveness |
|---|---|---|
| 6-Succinylamino nicotinamide | 7 | 4+ |
| 6-Glutarylamino nicotinamide | 5 | 3+ |
| 6-Maleylamino nicotinamide | 6 | 4+ |
| 6-Diphenylphosphorylamino nicotinamide | 7 | 4+ |
| 6-Methoxycarbamyl nicotinamide | 5 | 4+ |
| Methyl-1-methyl-6-keto-1,6-dihydronicotinate | 11 | 3+ |
| 1-Methyl-6-keto-1,6-dihydronicotinic acid | 5 | 3+ |
| 1-Methyl-6-keto-1,6-dihydronicotinamide | 4 | 3+ |

TABLE-continued

| Compound | Number of Patients | Therapeutic Effectiveness |
|---|---|---|
| 1-Methyl-6-amino-1,2-dihydronicotinamide | 5 | 4+ |
| 1-Phenyl-6-keto-1,6-dihydronicotinic acid | 3 | 3+ |

3+ Almost complete reduction of scale and erythema from lesions.
4+ Restoration to normal looking skin.

As shown by the above Table five compounds achieved a 4+ result, restoring normal looking skin in all patients tested. Five compounds achieved at least a 3+ result and succeeded in restoration of normal textured skin in that the lesions were still slightly erythematous.

Generally, the affected skin became less scaly and less erythematous after one week of topical treatment. The scaly and erythematous lesions ordinarily were substantially restored to normal appearing skin after two weeks of treatment. Improved states, comparable to normal skin were reached within two to three weeks after initiating treatment, and remained improved for several weeks up to several months, varying from patient to patient, without further application of the therapeutic composition.

As noted above, use of the compositions of this invention, however, do not result in a permanent cure. It has been observed that when regular application of a composition of this invention is terminated, normal appearing skin will remain for varying periods of time from a few weeks to several months depending upon the patient. However, when regular applications are resumed the lesions again disappear and normal appearing skin is restored.

In summary, this invention includes the discovery of compositions which are useful for alleviating the symptoms of psoriasis. The compositions may either be a cream, an ointment, a lotion or a gel of one or more of the above-described nicotinamide analogues. One or more of these compounds is present in the vehicle in a total concentration of from 0.01 to 5 percent by weight.

This invention may be embodied in other specific forms without departing from the spirit or essential characteristics thereof. The present embodiments are therefore to be considered in all respects as illustrative and not restrictive, the scope of the invention being indicated by the appended claims, and all changes which come within the meaning and range of equivalency of the claims are therefore intended to be embraced therein.

What is claimed is:

1. A composition useful in the treatment of psoriasis comprising: an antipsoriatic effective amount of a compound of the formula:

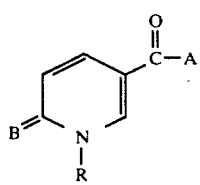

wherein
R is an alkyl or aryl radical having from 1 to 9 carbon atoms;
A is OH, or an alkoxy radical having from 1 to 9 carbon atoms; and
B is O in a pharmaceutically acceptable lotion, cream, or ointment for topical application.

2. The composition of claim 1 wherein said compound is present in said composition in a concentration of from 0.01 to 5 percent by weight.

3. The composition of claim 2, wherein said compound is present in a concentration of from 0.02 to 2 percent by weight.

4. The composition of claim 1 wherein said compound is 1-methyl-6-keto-1,6-dihydronicotinic acid.

5. The composition of claim 1 wherein said compound is methyl 1-methyl-6-keto-1,6-dihydronicotinate.

6. The composition of claim 1 wherein said compound is ethyl 1-methyl-6-keto-1,6-dihydronicotinate.

7. The composition of claim 1 wherein said compound is 1-phenyl-6-keto-1,6-dihydronicotinic acid.

8. The composition of claim 1 wherein said compound is methyl 1-phenyl-6-keto-1,6-dihydronicotinate.

9. The composition of claim 1 wherein said compound is ethyl 1-phenyl-6-keto-1,6-dihydronicotinate.

10. The composition of claim 1 wherein said compound is 1-benzyl-6-keto-1,6-dihydronicotinic acid.

11. The composition of claim 1 wherein said compound is methyl 1-benzyl-6-keto-1,6-dihydronicotinate.

12. The composition of claim 1 wherein said compound is ethyl 1-benzyl-6-keto-1,6-dihydronicotinate.

13. A method for treating the symptoms of psoriasis in humans comprising: topically applying to involved areas of the human body a therapeutically effective amount of a composition comprising an antipsoriatic effective amount of a compound having the formula

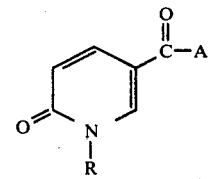

wherein
R is an alkyl or aryl radical having from 1 to 9 carbon atoms; and
A is OH or an alkoxy radical having from 1 to 9 carbon atoms in a pharmaceutically acceptable vehicle.

14. The method of claim 13 wherein said compound is present in said composition in a concentration of from 0.01 to 5 percent by weight.

15. The method of claim 13 wherein said compound is present in said composition in a concentration of from 0.02 to 2 percent by weight.

16. The method of claim 13 wherein said compound is 1 methyl-6-keto-1,6-dihydronicotinic acid.

17. The method of claim 13 wherein said compound is methyl 1-methyl-6-keto-1,6-dihydronicotinate.

18. The method of claim 13 wherein said compound is ethyl 1-methyl-6-keto-1,6-dihydronicotinate.

19. The method of claim 13 wherein said compound is 1-phenyl-6-keto-1,6-dihydronicotinic acid.

20. The method of claim 13 wherein said compound is methyl 1-phenyl-6-keto-1,6-dihydronicotinate.

21. The method of claim 13 wherein said compound is ethyl 1-phenyl-6-keto-1,6-dihydronicotinate.

22. The method of claim 13 wherein said compound is methyl 1-benzyl-6-keto-1,6-dihydronicotinate.

23. The method of claim 13 wherein said compound is ethyl 1-benzyl-6-keto-1,6-dihydronicotinate.

* * * * *